(12) United States Patent
Nakamura

(10) Patent No.: US 8,088,833 B2
(45) Date of Patent: Jan. 3, 2012

(54) METHOD FOR PURIFYING AN IGG MONOMER

(75) Inventor: Koji Nakamura, Shunan (JP)

(73) Assignee: Tosoh Corporation, Shunan-shi (JP)

( * ) Notice: Subject to any disclaimer, the term of this patent is extended or adjusted under 35 U.S.C. 154(b) by 447 days.

(21) Appl. No.: 12/226,597

(22) PCT Filed: Apr. 24, 2007

(86) PCT No.: PCT/JP2007/058879
§ 371 (c)(1),
(2), (4) Date: Oct. 23, 2008

(87) PCT Pub. No.: WO2007/123242
PCT Pub. Date: Nov. 1, 2007

(65) Prior Publication Data
US 2009/0234033 A1    Sep. 17, 2009

(30) Foreign Application Priority Data

Apr. 25, 2006 (JP) .................. 2006-120626

(51) Int. Cl.
*C07K 16/00* (2006.01)
*B01J 39/20* (2006.01)
*C08J 5/20* (2006.01)

(52) U.S. Cl. ............ 521/27; 521/25; 521/31; 530/387.1

(58) Field of Classification Search .................... 521/27, 521/31; 530/387.1
See application file for complete search history.

(56) References Cited

U.S. PATENT DOCUMENTS 5,258,503 A * 11/1993 Yokohari et al. .............. 530/415
5,453,186 A    9/1995 Muller et al.

FOREIGN PATENT DOCUMENTS

| EP | 0 306 617 A2 | 3/1989 |
| EP | 0 337 144 A1 | 10/1989 |
| JP | 59-206045 A | 11/1984 |
| JP | 64-68272 A | 3/1989 |
| JP | 1-119264 A | 5/1989 |
| JP | 1-310744 A | 12/1989 |
| WO | WO 99/62936 A | 12/1999 |
| WO | WO-2005/044856 A2 | 5/2005 |

OTHER PUBLICATIONS

Supplementary European Search Report issued in correponding European Application No. 07742314.3 dated Nov. 13, 2009.
John K. Lee, "Determination of the Molecular Size Distribution of Immunoglobulin G (IgG) in Intravenous IgG-Albumin Formulations by High-Performance Liquid Chromatography", Journal of Chromatography, vol. 444, p. 141-152, 1988.
Nadler et al., Rapid, automated, two-dimensional high-performance liquid chromatographic analysis of immunoglobulin G and its multimers, Journal of Chromatography A, vol. 676, p. 331-335, 1994.

* cited by examiner

*Primary Examiner* — Michael M Bernshteyn
(74) *Attorney, Agent, or Firm* — Birch, Stewart, Kolasch & Birch, LLP

(57) ABSTRACT

To provide a separating agent for IgG purification, whereby IgG can be separated and purified efficiently at a high purity, and a method for purifying an IgG using it.
A separating agent for IgG purification, characterized in that a polyacrylic acid and/or a polymethacrylic acid is immobilized on a carrier, and a method for purifying an IgG monomer, characterized in that a mixture containing an IgG monomer and an impurity containing polymeric IgG is contacted to the separating agent and eluted.

7 Claims, 2 Drawing Sheets

METHOD FOR PURIFYING AN IGG MONOMER

TECHNICAL FIELD

The present invention relates to a separating agent for IgG purification, its production method and a method for purifying an IgG monomer by using it. Specifically, the present invention relates to a separating agent which is used for removing impurities containing a dimmer to oligomer of IgG and/or aggregates of IgG (hereinafter, these are referred to as polymeric IgG) present in IgG elution fraction purified by protein A affinity chromatography or the like, from an IgG monomer; and a method for purifying an IgG monomer by using it.

BACKGROUND ART

IgG (immunoglobulin G) is useful as diagnostic agents and therapeutic agents, and its demand is expected to be increased. In order to use IgG for such applications, it is necessary to develop techniques to purify IgG at a high purity. In general, for the IgG purification, affinity chromatography using Protein A is used. Protein A is a protein isolated from the cell wall of Staphylococcus aureus and binds to IgG. Since Protein A binds IgG from many of mammalian species, and its binding capacity to IgG per unit protein is large, affinity chromatography which uses a carrier on which Protein A is immobilized is used for industrial antibody purification processes. However, since in the affinity chromatography which uses Protein A, an acidic solution having a pH of at most 4 is used for eluting adsorbed IgG, structure of antibody is likely to be denatured, and associated and aggregated. Further, aggregates are formed in a cell culture step, and it is difficult to remove impurities containing such polymeric IgG by the affinity chromatography using Protein A.

In order to solve the above problem, after the purification by the affinity chromatography using Protein A, a combined method of ion-exchange chromatography and hydrophobic interaction chromatography has been usually used. However, since in the conventional ion-exchange chromatography, separation of an IgG monomer from an impurity containing polymeric IgG is insufficient, a yield of IgG is required to be sacrificed, in order to obtain high purity IgG (namely IgG monomer). Further, in the hydrophobic interaction chromatography, there are problems that a recovery rate is low, and long time is required, which lead to high cost.

On the other hand, various separating agents wherein a polyanion is immobilized on a carrier have been proposed. For example, as a low specific density lipoprotein adsorbing material, an adsorbing material having a high molecule polyanion part having a molecular weight of at least 25,000 on its surface has been known (for example, Patent Document 1). Further, as an adsorbing material for immune complexes, an adsorbing material wherein a compound having an anionic functional group is immobilized on a water-insoluble porous carrier has been known (for example, Patent Document 2). However, in these documents, separating and purifying only an IgG monomer from a mixture containing an IgG monomer and polymeric IgG is not disclosed.

Further, as a separation material for biopolymers (macromolecules), a separation material covered with a polymer wherein surfaces of supporting particles having a hydroxyl group are covalent bonded, has been known (for example, Patent Document 3). In Example E of Patent Document 3, immunoglobulin (IgG) in human serum is separated, however, separating and purifying only an IgG monomer at a high purity is not disclosed. Further, with said separation material, it is difficult to control the molecular weight, molecular weight distribution and graft density (surface density of a graft chain) of a graft chain and the molecular weight of a polymer present on a carrier is low, and therefore, it is considered that separation of an IgG monomer from polymeric IgG would be insufficient.

As mentioned above, in order to use IgG widely as diagnostic agents and therapeutic agents, mass production of a high purity IgG monomer at low cost is necessary. However, there are many unsolved problems in conventional techniques, and in order to solve such problems, development of a novel separating agent and a method for purifying an IgG monomer has been desired.

Patent Document 1: JP-A-59-206045 (claim 1)
Patent Document 2: JP-A-1-68272 (claim 1)
Patent Document 3: JP-1-310744 (claim 1, page 9, upper right column, lines 15 to 19, page 12, lower left column, lines 13 to 20)

DISCLOSURE OF THE INVENTION

Problems to be Solved by the Invention

In order to solve the above problems, it is an object of the present invention to provide a separating agent for IgG purification, whereby IgG can be purified efficiently at a high purity, and a method for purifying an IgG monomer, which employs it.

Means of Solving the Problems

As a result of extensive studies to solve the above problems, the present inventors have found that by a separating agent, wherein a polyacrylic acid and/or a polymethacrylic acid is immobilized on a carrier, an IgG monomer can be separated from polymeric IgG under a mild condition, and the above problems can be solved all at once. Thus, the present invention has been accomplished.

Namely, the present invention is a separating agent for IgG purification and a method for purifying IgG using it, as described below.

(1) A separating agent for IgG purification, which comprises a carrier and a polyacrylic acid and/or a polymethacrylic acid immobilized on the carrier.
(2) The separating agent according to the above (1), wherein the polyacrylic acid and/or the polymethacrylic acid is dispersed and immobilized on multipoints on a surface of the carrier.
(3) The separating agent according to the above (1) or (2), wherein the polyacrylic acid and/or the polymethacrylic acid has a viscosity average molecular weight of at least 5,000.
(4) The separating agent according to any one of the above (1) to (3), wherein the carrier is a porous carrier.
(5) The separating agent according to the above (4), wherein the porous carrier is at least one member selected from the group consisting of an inorganic material, a polysaccharide and a synthetic polymer.
(6) The separating agent according to any one of the above (1) to (5), wherein the carrier is in the form of spherical particles, non-spherical particles, a membrane or a monolith (continuum).
(7) A method for purifying an IgG monomer, in which a mixture containing an IgG monomer and impurities is contacted to the separating agent as defined in any one of the above (1) to (6) for elution.

(8) The method according to the above (7), wherein the impurities contain a dimmer or oligomer of IgG and/or aggregates of IgG (namely polymeric IgG).

(9) The method according to the above (7) or (8), wherein the elution method is a method wherein the eluant salt concentration or the eluant pH is linearly increased, and IgG adsorbed on the separating agent is eluted; a method wherein the eluant salt concentration or the eluant pH is stepwise increased, and IgG adsorbed on the separating agent is eluted; or a method wherein without having the IgG monomer adsorbed on the separating agent, only polymeric IgG is adsorbed thereon.

Effect of the Invention

By using the separating agent for IgG purification of the present invention, from a mixture containing an IgG monomer and impurities containing polymeric IgG, the impurities can be separated efficiently, and the desired IgG monomer can be purified at a high purity.

BEST MODE FOR CARRYING OUT THE INVENTION

Figure 1:
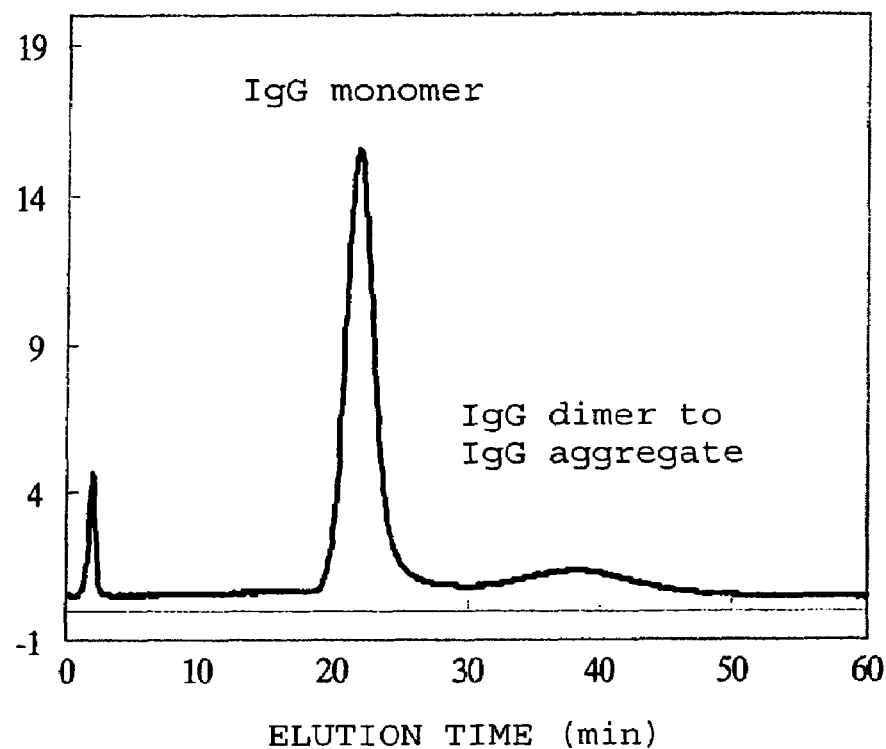
FIG. 1 is a chromatogram which shows the separation result of human monoclonal antibody described in Example 5.

The separating agent for IgG purification in the present invention is a separating agent characterized in that a polyacrylic acid and/or a polymethacrylic acid is immobilized on a carrier.

Purification of an IgG monomer with the separating agent of the present invention is mainly based on an electrostatic interaction between IgG and the separating agent. As mentioned above, a method for removing lipoproteins in blood with an adsorbing material having a high molecule polyanion part has been proposed. However, this method is based on biological affinity between lipoproteins and the adsorbing material, and its separation mechanism is different from that of the present invention. In the separating agent of the present invention, since the polyacrylic acid and/or the polymethacrylic acid has a function to adsorb IgG, it is necessary to immobilize a polyacrylic acid and/or a polymethacrylic acid on a surface of the separating agent. Further, in consideration of separation properties, preferred is the separating agent wherein the polyacrylic acid and/or the polymethacrylic acid is dispersed and immobilized on multipoints on a surface of the carrier in the present invention.

In the separating agent of the present invention, the polyacrylic acid and/or the polymethacrylic acid to be immobilized on a carrier has a viscosity average molecular weight of from 5,000 to 1,000,000. Particularly, as the viscosity average molecular weight increases, the separation degree of an IgG monomer from polymeric IgG is improved.

In the separating agent of the present invention, the material and porosity of the inside of the separating agent, which does not contact to IgG do not directly is relate to the separation mechanism of the electrostatic interaction of the present invention, and therefore, either a non-porous material or a porous material may be used as a carrier. From the practical viewpoint, however, since it is desired to treat a large amount of IgG in one operation for time and cost, it is preferred to increase the surface area of the separating agent by preparing the separating agent from a porous carrier, and a separating agent having a relative surface area of at least 1 $m^2/g$ is more preferred.

As the porous carrier used in the separating agent of the present invention, a known carrier useful as a packing material for column chromatography can be used without specific limitations. For example, an inorganic porous material such as porous glass or porous silica gel, a polysaccharide such as agarose, dextran or celluolose, a synthetic polymer such as a polyacrylamide, a polymethylmethacrylate, a polyvinyl alcohol or a styrene-divinyl benzene copolymer may preferably be mentioned. In a case where the separating agent of the present invention is used industrially, the separating agent is alkali-washed after purification operation, and therefore, among the above carriers, a carrier made of the polysaccharide or the synthetic polymer, which has resistance to an alkali, is preferred. Further, the form of the carrier is not particularly limited, however, non-spherical particles, a membrane or a monolith (continuum) may, for example, be mentioned.

The form of the separating agent of the present invention varies depending on conditions for use and is not particularly limited. However, for example, in a case where it is used as a packing material for column chromatography, the separating agent in the form of particles is preferred, and in order to pack a column with the separating agent uniformly, the form of spherical particles is more preferred. Further, a column may be provided with a porous body of the separating agent in the form of continuous united monolith. Further, chromatography employing the separating agent in the form of a membrane may be used.

In a case where the separating agent is used in the form of spherical particles, the particle size of the separating agent can be preferably selected, depending on conditions for use, and it is not particularly limited. However, for example, in a case where the separating agent in the form of spherical particles is used as a packing material for HPLC, the average particle size is usually from 5 to 15 μm, in a case of a preparative isolation for a small amount of the desired product, it is preferably from 15 to 50 μm, and in a case of an industrial process, it is preferably from 50 to 300 μm.

In the present invention, the method to immobilize a polyacrylic acid and/or a polymethacrylic acid on a carrier is not particularly limited, and conventional methods may be employed. For example, it is possible to employ a method wherein an epoxy group is introduced on a carrier surface by applying epichlorohydrin, a polyfunctional epoxy compound or the like on the carrier surface, and then a polyacrylic acid and/or a polymethacrylic acid is reacted; or a method wherein after introducing an epoxy group, ammonia or the like is used for amination, and an amino group is bound to a carboxyl group of a polyacrylic acid and/or a polymethacrylic acid with a carbodiimide reagent, etc.

The method of the present invention for purifying an IgG monomer, is characterized in that a mixture purified by Protein A affinity chromatography or the like and containing an IgG monomer and impurities containing polymeric IgG is contacted to the separating agent of the present invention and eluted.

The type of IgG purified by the method of the present invention may be either polyclonal antibody or monoclonal antibody.

In the purification of the present invention, the method to contact the mixture containing an IgG monomer and impurities containing polymeric IgG to the separating agent of the present invention is not particularly limited, and a method employing conventional ion exchange chromatography may, for example, be used. Namely, the mixture is adsorbed to the separating agent of the present invention in a buffer and then eluted, whereby the IgG monomer can be separated from the impurities containing polymeric IgG.

In the purification method of the present invention, the method to elute IgG adsorbed on the separating agent of the present invention is not particularly limited. For example, it is possible to employ a method wherein the eluant salt concentration or the eluant pH is linearly increased, and IgG adsorbed on the separating agent is eluted (linear gradient elution); or a method wherein the eluant salt concentration or the eluant pH is stepwise increased, and IgG adsorbed on the separating agent is eluted (stepwise gradient elution). Further, it is possible to employ a method wherein the eluant salt concentration is preliminarily increased, and wherein without having the IgG monomer adsorbed on the separating agent, only polymeric IgG is adsorbed thereon.

EXAMPLES

Now, the present invention will be explained in further detail with reference to Examples. However, the present invention is by no means restricted to such specific Examples.

Example 1

100 g of epichlorohydrin and an aqueous NaOH solution (NaOH: 40 g, $H_2O$: 180 g) were added to 100 ml of a packing material for gel filtration chromatography wherein a base material is a hydrophilic vinyl polymer (trade name: TOYO PEARL HW-65C, manufactured by TOSOH CORPORATION, the exclusion limit determined using proteins is $5 \times 10^6$, particle size: 50 to 100 µm) and reacted at 400° C. for 4 hours to obtain an epoxidized gel. 100 ml of a dense ammonia water was added to the gel, followed by stirring at 50° C. for 2 hours to obtain an amino group-containing gel having an amino group introduced.

Then, 2 g of a polyacrylic acid (viscosity average molecular weight: 5,000) was dissolved in 100 ml of water, and 100 ml of the amino group-containing gel was added thereto. 2 g of 1-ethyl-3-(dimethylaminopropyl)-carbodiimide maintained at pH 4.5 was added to the above solution at 4° C., followed by stirring at the same temperature for 24 hours. After the termination of the reaction, the product was washed with 0.5 mol of a saline solution and then washed with water to obtain a polyacrylic acid immobilized gel of the present invention. The amount of the fixed polyacrylic acid was 4 mg/ml.

Example 2

The same reaction was carried out as in Example 1 except that a polyacrylic acid (viscosity average molecular weight: 250,000) was used, to obtain a separating agent of the present invention. The amount of the polyacrylic acid introduced was 5 mg/ml.

Example 3

2 g of a polyacrylic acid (viscosity average molecular weight: 5,000) was dissolved in 100 ml of water, and then 100 ml of an agarose gel in which an amino group is preliminarily introduced (trade name: EAH-Sepharose 4b, manufactured by GE Healthcare UK Ltd., particle size: 45 to 165 µm) was added thereto. 2 g of 1-ethyl-3-(dimethylaminopropyl)-carbodiimide maintained at pH 4.5 was added to the above solution at 4° C., followed by stirring at the same temperature for 24 hours. After the termination of the reaction, the product was washed with 0.5 mol of a saline solution and then washed with water to obtain a polyacrylic acid immobilized gel of the present invention. The amount of the immobilized polyacrylic acid was 6 mg/ml.

Example 4

An aqueous solution prepared by dissolving 2 g of a polymethacrylic acid in 100 ml of water was added to 100 ml of the epoxidized gel obtained in Example 1 and reacted at 40° C. for 16 hours. After the termination of the reaction, the product was washed with 0.5 mol of a saline solution and then washed with water to obtain a polyacrylic acid immobilized gel as the separating agent of the present invention. The amount of the immobilized polymethacrylic acid was 4 mg/ml.

Example 5

A column having an inner diameter of 6 mm and a length of 4 cm was packed with the separating agent obtained in Example 1, and a human monoclonal antibody was injected into the column. Then, a mixture containing an IgG monomer and an impurities containing polymeric IgG (dimmer to an aggregate of IgG) was separated by the method wherein the eluant salt concentration or the eluant pH was linearly increased (linear gradient). The obtained chromatogram is shown in FIG. 1.

Specifically, the separation of the IgG monomer from the polymeric IgG by the separating agent of the present invention obtained in Example 1 was carried out by the following method. Namely, a column (inner diameter: 6 mm, length: 4 cm) was packed with the separating agent obtained in Example 1 and connected to an FPLC apparatus (Akta Prime, manufactured by GE Healthcare). The column was equilibrated with ten column volume of 50 mM phosphate buffer (pH 6.0) at a flow rate of 0.5 ml/min. Then, a human monoclonal antibody (100 µg) was injected. A 50 mM phosphate buffer containing 1M NaCl was used for the elution, and the separation was carried out by the linear salt concentration gradient elution method for 60 minutes. In FIG. 1, the abscissa shows the retention time (minute), and the peak eluted around 22 minutes is a peak of an IgG monomer, and the peak eluted around 38 minutes is a peak of polymeric IgG.

Example 6

Figure 2:
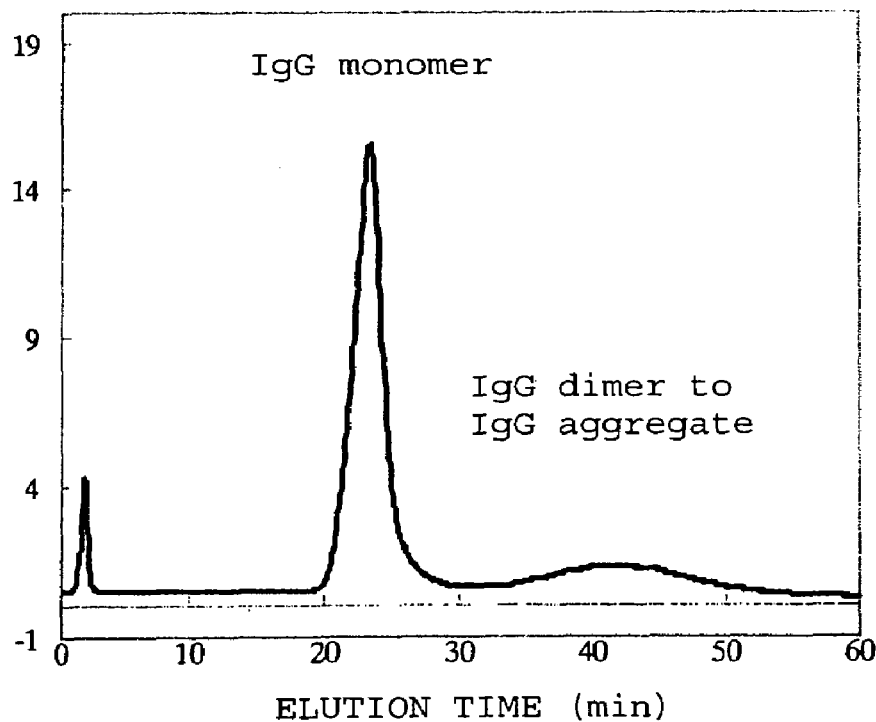
FIG. 2. is a chromatogram which shows the separation result of human monoclonal antibody described in Example 6.

The separation of a mixture containing an IgG monomer and polymeric IgG was carried out under the same separation conditions as in Example 5, except that the separating agent obtained in Example 2 was used. The obtained chromatogram is shown in FIG. 2. In FIG. 2, the peak eluted around 23 minutes is a peak of an IgG monomer, and the peak eluted around 42 minutes is a peak of polymeric IgG.

Comparative Example 1

Figure 3:
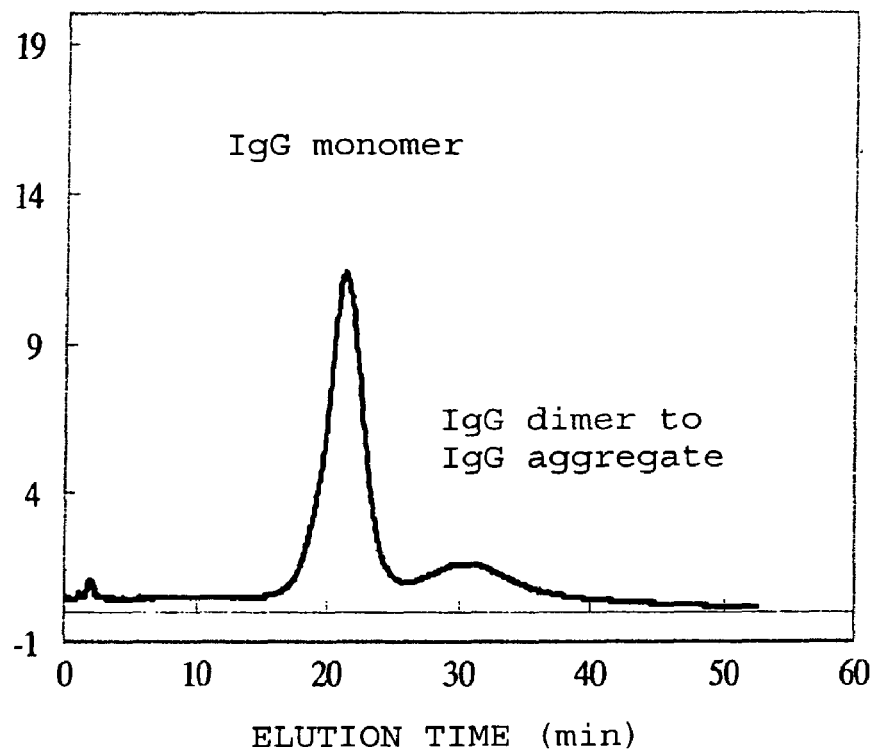
FIG. 3. is a chromatogram which shows the separation result of human monoclonal antibody described in comparative Example 3.

The separation of a mixture containing an IgG monomer and polymeric IgG was carried out under the same separation conditions as in Example 5, except that as a separating medium, TOYO PEARL CM-650 (trade name, manufactured by TOSOH CORPORATION) wherein a carboxymethyl group is introduced into TOYO PEARL HW-65C, was used. The obtained chromatogram is shown in FIG. 3. In FIG. 3, the peak eluted around 22 minutes is a peak of an IgG monomer, and the peak eluted around 30 minutes is a peak of polymeric IgG.

By comparing FIGS. 1, 2, and 3, it is clear that by using the separating agent of the present invention, the separation degree of an IgG monomer from polymeric IgG is remarkably improved, and a high purity IgG monomer can be obtained, as compared to a conventional cation exchanger (TOYO PEARL CM-650).

Comparative Example 2

Figure 4:
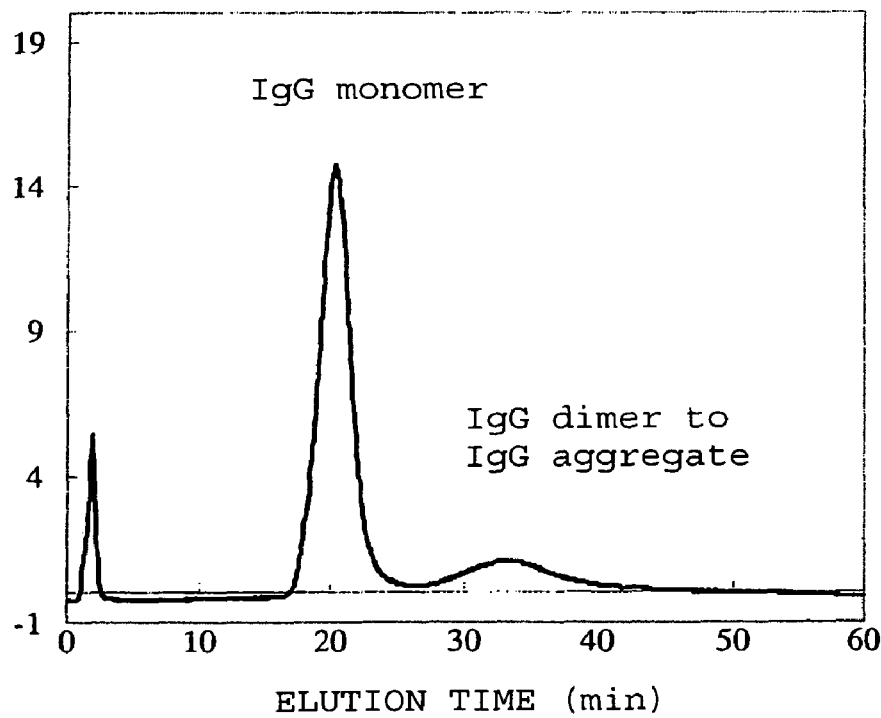
FIG. 4. is a chromatogram which shows the separation result of human monoclonal antibody described in Comparative Example 2.

The separation of a mixture containing an IgG monomer and polymeric IgG was carried out under the same separation conditions as in Example 5, except that as a separating agent, Fractogel EMD COO⁻ (trade name, manufactured by Merck Ltd.) which is a separating agent wherein an acrylic acid is graft polymerized to a carrier, was used. The obtained chromatogram is shown in FIG. 4. In FIG. 4, the peak eluted around 20 minutes is a peak of an IgG monomer, and the peak eluted around 33 minutes is a peak of polymeric IgG.

By comparing FIGS. 1, 2, and 4, it is clear that by using the separating agent of the present invention, an IgG monomer can be efficiently separated and purified, as compared to a separating agent disclosed in Patent Document 3 (Fractogel EMD COO⁻).

INDUSTRIAL APPLICABILITY

According to the present invention, it is possible to solve problems in an ion-exchange chromatography method commonly used for further purification, after Protein A affinity chromatography purification, such that separation of an IgG monomer from an impurity containing polymeric IgG is insufficient, the recovery rate of IgG is low, and cost is high since long time is required, and therefore, industrial applicability as a separating agent for IgG purification is high.

The entire disclosure of Japanese Patent Application No. 2006-120626 filed on Apr. 25, 2006 including specification, claims and summary is incorporated herein by reference in its entirety.

The invention claimed is:

1. A method for purifying an IgG monomer, comprising:
contacting a mixture containing an IgG monomer and impurities with a separating agent to absorb IgG on the separating agent, wherein the separating agent comprises a carrier and a polyacrylic acid and/or a polymethacrylic acid immobilized on the carrier, and wherein the impurities contain a dimer or oligomer of IgG and/or aggregates of IgG; and eluting IgG absorbed on the separating agent, wherein an eluent salt concentration or an eluent pH is linearly or stepwisely increased so that IgG adsorbed on the separating agent is eluted.

2. The method for purifying an IgG monomer according to claim 1, wherein the polyacrylic acid and/or the polymethacrylic acid is dispersed and immobilized on multipoints on a surface of the carrier.

3. The method for purifying an IgG monomer according to claim 1, wherein the polyacrylic acid and/or the polymethacrylic acid has a viscosity average molecular weight of at least 5,000.

4. The method for purifying an IgG monomer according to claim 1, wherein the carrier is a porous carrier.

5. The method for purifying an IgG monomer according to claim 1 wherein the porous carrier is at least one member selected from the group consisting of an inorganic material, a polysaccharide and a synthetic polymer.

6. The method for purifying an IgG monomer according to claim 1, wherein the carrier is in the form of spherical particles, non-spherical particles, a membrane or a monolith continuum.

7. The method according to claim 1, wherein only polymeric IgG is adsorbed on the separating agent, without having the IgG monomer adsorbed on the separating agent.

* * * * *